United States Patent [19]

Shimizu et al.

[11] Patent Number: 4,855,519
[45] Date of Patent: Aug. 8, 1989

[54] METHOD FOR PRODUCING ARYLETHYLENE

[75] Inventors: Isoo Shimizu, Yokohama; Hitoshi Mitsuyuki, Kawasaki; Kazumichi Uchida; Yuuichi Tokumoto, both of Yokohama, all of Japan

[73] Assignee: Nippon Petrochemicals Company, Tokyo, Japan

[21] Appl. No.: 271,219

[22] Filed: Nov. 14, 1988

[30] Foreign Application Priority Data

Nov. 12, 1987 [JP] Japan .............................. 62-285899
Nov. 12, 1987 [JP] Japan .............................. 62-285900

[51] Int. Cl.$^4$ ............................................. C07C 4/24
[52] U.S. Cl. ................................. 585/319; 585/320; 585/321; 585/426; 585/439; 585/446; 585/456
[58] Field of Search ............... 585/3.9, 320, 321, 439, 585/426, 446, 454

[56] References Cited

U.S. PATENT DOCUMENTS

| | | | |
|---|---|---|---|
| 3,062,903 | 11/1962 | Odioso et al. | 585/439 |
| 3,441,625 | 4/1969 | Bergeron et al. | 585/439 |
| 4,070,366 | 1/1978 | Gregorovich et al. | 585/454 |
| 4,694,100 | 9/1987 | Shimizu et al. | 560/105 |

*Primary Examiner*—Curtis R. Davis
*Attorney, Agent, or Firm*—Scully, Scott, Murphy & Presser

[57] ABSTRACT

A method for producing arylethylene comprising four steps of: (I) bringing 1,1-diarylethane into contact with an acid catalyst in the presence of an inert gas to crack said compound into arylethylenes and alkylbenzenes; (II) separating the reaction mixture obtained in the above cracking step (I) into at least a fraction mainly containing 1,1-diarylethane; (III) bringing said fraction mainly containing 1,1-diarylethane into contact with hydrogen gas in the presence of a hydrogenation catalyst; and (IV) re-cracking hydrogenated fraction obtained in the preceding hydrogenation step (III) by bringing it into said cracking step (I).

Particularly, this method is useful for producing p-isobutylstyrene which is a starting material for preparing a valuable medicine of ibuprofen.

12 Claims, No Drawings

METHOD FOR PRODUCING ARYLETHYLENE

BACKGROUND OF THE INVENTION

1. Field of the Invention

This invention relates to a method for producing arylethylene. More particularly, the invention relates to a method for economically producing highly pure arylethylene, preferably p-isobutylstyrene, etc. in an industrial scale. Furthermore, the present invention relates to a method for producing highly pure arylethylene which comprises the steps of: cracking diarylethane, separating the cracking products, hydrogenating the recovered fraction mainly containing unreacted diarylethane, and cracking again the recovered hydrogenated diarylethane fraction generally by recycling it to the above cracking step. A preferable compound that is prepared according to the method of the present invention is p-isobutylstyrene. This compound is well known as a useful intermediate material for preparing ibuprofen (tradename, α-(4-isobutylphenyl)propionic acid) which is a medicine used for the relief of fever, pain and inflammation.

2. Description of the Prior Art

In connection with the preparation of arylethylene such as p-isobutylstyrene by cracking 1,1-diarylethane in the presence of an acid catalyst, various kinds of methods have been hitherto proposed. For example, Ind. Eng. Chem., Vol. 46, No. 4, 652 (1954), J. Chem. Eng. Data, Vol. 9, No. 1, 104 (1964) and I & EC Prod. Res. Dev., Vol. 3, No. 1, 16 (1964).

It is disclosed in the above references that alkylstyrenes such as methylstyrene and dimethylstyrene are obtained by cracking 1,1-diarylethanes such as 1,1-ditolylethane and 1,1-dixylylethane. Furthermore, they refer to the preparation of ethylstyrene, isopropylstyrene and tert-butylstyrene.

There are more definite references on the improvement in cracking catalysts:

U.S. Pat. No. 2,420,689: Method for preparing dimethylstyrene by cracking dixylylethane in the presence of kaolin catalyst U.S. Pat. No. 2,422,318: Method for cracking asymmetric diarylethanes U.S. Pat. No. 2,864,872: Method for using silica as a cracking catalyst U.S. Pat. No. 2,954,413: Method for cracking dixylylethane using fluidized catalyst U.S. Pat. No. 3,025,330: Method for preparing methylstyrene from ditolylethane U.S. Pat. Nos. 2,976,333 and 2,976,334: Method for improving cracking catalyst In the cracking of 1,1-diarylethane, all the 1,1-diarylethane is not converted into arylethylene (alkylstyrene) and alkylbenzene but unreacted 1,1-diarylethane is inevitably contained in the reaction mixture. This fact is apparent from the description of the above references that the conversion per one pass is 40 to 60%. In other words, unreacted starting material as much as 60 to 40% remains in the reaction product.

This fact is the same in the case of the cracking of 1,1-bis(4-isobutylphenyl)ethane and it was found out by the inventors of this application that the average cracking rate is in the range of 40 to 60%. In other words, unreacted 1,1-bis(4-isobutylphenyl)ethane as much as 40 to 60% remains.

Accordingly, in order to prepare economically arylethylene by the cracking of 1,1-diarylethane, it is inevitable to reuse and crack again the unreacted 1,1-diarylethane. In other words, when the fraction mainly containing 1,1-diarylethane is separated from the reaction mixture and used again for cracking, the industrial applicability of the cracking reaction depends upon the possibility to obtain arylethylene having a purity and properties which are suitable for the purpose of industrial uses.

Incidentally, arylethylenes obtained by cracking 1,1-diarylethanes have various uses, including aforesaid medicine, such as:

industrially useful intermediates proposed in West German Offenlegungsschrift No. 2 325 302 and British Pat. No. 1,565,235; and raw material for the synthesis of weatherproof polymer disclosed in Ind. Eng. Chem., Vol. 46, 652 (1954). Therefore, the proposal of economical preparation of arylethylene has been wanted.

The present inventors made investigation into the economical and industrial working of the cracking of 1,1-diarylethane. As a result, it was found out that, when the fraction mainly containing unreacted 1,1-diarylethane is simply cracked again, the deterioration of cracking catalyst is severe with the passage of time and the properties of obtained arylethylene are not satisfactory.

That is, the present inventors noticed as a result of the cracking of 1,1-diarylethane that diarylethylenes having boiling points close to that of 1,1-diarylethane and being difficultly separated, are generated, and that the fraction mainly containing 1,1-diarylethane cannot be prevented from containing the olefins. In addition, when this fraction is brought back to the cracking step and cracked again, because the material to be cracked contains diarylethylenes, complicated cracking product is obtained. Accordingly, a vicious circle is caused to occur in that the side reaction products of this re-cracking also have boiling points close to that of the aimed arylethylene, as a result, the contamination with the by-product in the aimed arylethylene fraction cannot be avoided. Therefore, it has not been possible to reuse a large quantity of unreacted 1,1-diarylethane fraction intact and thus, the conventional method for preparing arylethylene by cracking 1,1-diarylethane has not been economical method in view of industrial practice.

BRIEF SUMMARY OF THE INVENTION

In view of the above-described background, the object of the present invention to provides an improved method for producing arylethylene which method comprises the following steps:

step (I): bringing 1,1-diarylethane represented by the following general formula (A) into contact with an acid catalyst in the presence of an inert gas to crack said 1,1-diarylethane into arylethylenes represented by the general formulae (B) and/or (C) and alkylbenzenes represented by the general formulae (D) and/or (E);

step (II): separating the reaction mixture obtained in the above cracking step (I) into at least a fraction mainly containing 1,1-diarylethane of the general formula (A);

step (III): bringing the fraction mainly containing 1,1-diarylethane of the general formula (A) into contact with hydrogen gas in the presence of a hydrogenation catalyst to hydrogenate diarylethylenes contained therein into 1,1 diarylethane; and step (IV): re-cracking the hydrogenated fraction obtained in the preceding hydrogenation step (III) by bringing it into the cracking step (I).

General formula (A): $Ar_1$—$CH(CH_3)$—$Ar_2$
General formula (B): $Ar_1$—$CH=CH_2$
General formula (C): $Ar_2$—$CH=CH_2$
General formula (D): $Ar_1$—H
General formula (E): $Ar_2$—H In the above formulae (A), (B), (C), (D), and (E), each of $Ar_1$ and $Ar_2$ is a phenyl group or an alkylphenyl group having a hydrogen atom or one or more of the same or different alkyl groups having 4 or less carbon atoms and the total number of carbon atoms is 4 or less. $Ar_1$ and $Ar_2$ can be the same or different ones.

It is important to hydrogenate by-product diarylethylenes such as bis(isobutylphenyl)ethylene in the above step (III).

In the case of the preparation of preferable p-isobutylstyrene, both the $Ar_1$ and $Ar_2$ in the above formulae (A), (B). (C), (D), and (E) are p-isobutylphenyl groups. In other words, the general formula (A) is 1,1-bis(4-isobutylphenyl)ethane, the general formulae (B) and (C) are p-isobutylstyrene and the general formulae (D) and (E) are isobutylbenzene.

As described above, the method for producing arylethylene according to the present invention comprises the above steps (I), (II), (III) and (IV), and the method enables the industrial and economical preparation of highly pure arylethylene by the cracking of 1,1-diarylethane.

DETAILED DESCRIPTION OF THE INVENTION

In the step (I) in the method of the present invention, 1,1-diarylethane is brought into contact with an acid catalyst in the presence of an inert gas to crack it into arylethylene and alkylbenzene. Conventional cracking methods and crackers can be used for this cracking step (I).

1,1-Diarylethane is a compound in which one carbon atom of ethane has substituent groups of two phenyl or alkylphenyl groups which have a hydrogen atom or alkyl groups having 4 or less carbon atoms, where the total number of carbon atoms in the alkyl groups is 4 or less. These substituent groups may be the same or different ones. Furthermore, when the substituent alkyl groups are plural, they can be the same or different.

Any of 1,1-diarylethanes produced by the conventional methods can be used as starting materials. Preparation of 1,1-diarylethane is exemplified by such processes that polyalkylbenzene is reacted with acetaldehyde or acetylene in the presence of sulfuric acid; polyalkylbenzene is reacted with 1,1-dichloroethane in the presence of a Friedel-Crafts catalyst such as aluminum chloride; and polyalkylbenzene is reacted with alkylstyrene in the presence of an acid catalyst. Furthermore, the fraction mainly containing diphenylethane and ethyl-diphenylethane which is obtained from the heavy by-product oil in the preparation of ethylbenzene for producing styrene, can also be used.

Among 1,1-diarylethanes which can be used in the method of the present invention, symmetrical compounds are exemplified by: 1,1-diphenylethane, 1,1-ditolylethane, 1,1-dixylylethane, 1,1-bis(ethylphenyl)ethane, 1,1-bis(tolylmethylphenyl)ethane, 1,1-bis(methylethylphenyl)ethane, 1,1-bis(propylphenyl)ethane, 1,1-bis(tetramethylphenyl)ethane, 1,1-bis(dimethylethylphenyl)ethane, 1,1-bis(methylpropylphenyl)ethane, 1,1-bis(diethylphenyl)ethane, 1,1-bis(n-butylphenyl)ethane, 1,1-bis(iso-butylphenyl)ethane, 1,1-bis(tert-butylphenyl)ethane and a preferable material of 1,1-bis(4-isobutylphenyl)ethane.

In the step (I) of the method of the present invention, it is desirable that the contact with an acid catalyst is carried out in a diluted condition in the coexistence of an inert gas. Any of inert gases, for example, inorganic gases such as hydrogen, helium, argon, nitrogen and steam; hydrocarbons such as methane, ethane and propane can be used unless it does not inhibit the acidic activity of an acid catalyst. The inert gases can be used either singly or as a mixture of them. In industrial practice, steam is preferable in view of its easiness in handling. In the dilution with an inert gas, the molar ratio in terms of: (inert gas/1,1-diarylethane) is desirably 50 or higher. There is no upper limit of this molar ratio of dilution, and the higher the better. However, a molar ratio of 500 is the upper limit in practical viewpoint.

The acid catalysts to be used in the catalytic cracking are protonic acids, inorganic solid acids, or protonic acids carried on a inorganic solid acid. The protonic acids are exemplified by inorganic protonic acids such as phosphoric acid, sulfuric acid, hydrochloric acid and heteropoly-acids such as silicotungstic acid and phosphotungstic acid, and organic protonic acids such as benzenesulfonic acid and toluenesulfonic acid. The inorganic solid acids are exemplified by synthetic solid acid catalysts such as silica-alumina, silica-magnesia and zeolite, natural solid acid substances such as activated clay, acid clay, kaolin and attapulgite, and protonic acid catalysts carried on solid acids in which an inorganic porous carrier such as non-acidic silica or alumina is impregnated with the foregoing protonic acid.

The temperature of contact with an acid catalyst can be arbitrary selected according to the kind of acid catalyst, however, it comes within a range of 200° C. to 650° C. In the contact with a protonic acid, temperatures in the range of 200° C. to 350° C. are preferable, meanwhile, in the contact with a solid acid, temperatures in the range of 300° C. to 600° C. are preferable.

In the cracking step (I) of the present invention, 1,1-diarylethane is cracked by being brought into contact with an acid catalyst under the foregoing dilution condition and temperature condition. The method of cracking can be selected according to the kind of acid catalyst. In view of the continuous operation and the corrosion inhibition of apparatus, gas phase contact with a solid acid catalyst or a protonic acid catalyst carried on a solid acid is desirable. In the gas phase contact, as far as 1,1-diarylethane is maintained in a gas phase under diluted condition, any of atmospheric pressure, elevated pressure and reduced pressure can be employed. With regard to the type of reaction, any of fixed bed, moving bed and fluidized bed can be employed.

The cracking reaction of step (I) is represented by the chemical equations as follows:

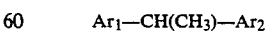
$Ar_1$—$CH(CH_3)$—$Ar_2$ when it is cracked in the right moiety:

→$Ar_1$—$CH=CH_2$+H—$Ar_2$ when it is cracked in the left moiety:

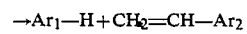
→$Ar_1$—H+$CH_2=CH$—$Ar_2$

Accordingly, a symmetrical 1,1-diarylethane, i.e. when the groups Ar₁ and Ar₂ are the same, a single kind of arylethylene (Ar—CH=CH₂) and a single kind of alkylbenzene (Ar—H) are obtained. Therefore, in many cases, it is desirable to use a symmetrical 1,1-diarylethane as a material to be decomposed. More particularly, this is exemplified by the preparation of p-isobutylstyrene by means of chemical equation as follows:

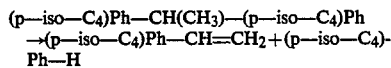

wherein iso—C₄ is an isobutyl group and Ph is a phenyl group.

In the step (II) of the method of the present invention, the reaction mixture obtained in the cracking step (I) is separated into at least a fraction mainly containing 1,1-diarylethane.

Incidentally, it is not always necessary that the aimed arylethylene is separated in the step (II) because alkylbenzene can be contained according to the kind of reaction using the arylethylene as a starting material. Therefore, in the step (II), arylethylene may be separated as a fraction mainly containing arylethylene or a fraction containing arylethylene and alkylbenzene. They can be used intact as the reaction material in the next step or arylethylene can be separated by an arbitrary separation means. Furthermore, this fact is applied also to alkylbenzene.

All the 1,1-diarylethane is not cracked in the step (I), so that unreacted 1,1-diarylethane remains in the cracking product together with the aimed arylethylene and alkylbenzene. It is important in the industrial practice that the unreacted 1,1-diarylethane is so separated as to be used again for cracking.

That is, in the separation step (II), at least a raw material fraction to be recovered and reused as an unreacted compound of Ar₁CH(CH₃)Ar₂ of the general formula (A) is separated.

As the separation method, any of conventional physical means and chemical means can be selected. For example, the physical means are exemplified by separation by solvent extraction utilizing the differences in solubilities or distribution coefficients, separation by adsorption utilizing the difference in adsorbing properties, separation by crystallization utilizing the difference in melting points or freezing points, and separation by distillation utilizing the difference in boiling points.

Among these separation methods, the distillation, especially reduced pressure distillation, is most preferable in view of its easiness in operation. The alkylbenzene, arylethylene and 1,1-diarylethane in the reaction mixture obtained in the step (I) of the present invention can be easily separated by conventional distillation method. It is preferable that the distillation operation is done under a reduced pressure because the aimed product is arylethylene which is liable to polymerize thermally.

In the case of arylethylene with an alkyl group having 5 or more carbon atoms or alkyl groups having 5 or more carbon atoms in total, the boiling point is high even when the distillation pressure is lowered, in which the loss due to thermal polymerization increases. In other words, the advantageous separation by distillation cannot be employed for such a heavier alkylstyrene.

It has been found out by the inventors that, when the fraction separated in the step (II) mainly containing 1,1-bis(p-isobutylphenyl)ethane is recycled intact and cracked again in the step (I), the deterioration of cracking catalyst occurs rapidly and that properties of obtained p-isobutylstyrene are not suitable for practical uses. In order to solve this problem, the present invention was accomplished.

In other words, in the cracking step (I), it became clear that the ethane moiety of starting 1,1-bis(p-isobutylphenyl)ethane is dehydrogenated by the cracking catalyst. Though it occurs slightly, the compound is converted into olefin as the equation below and the formation of 1,1-bis(p-isobutylphenyl)ethylene cannot be avoided.

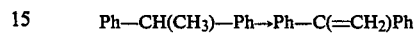

Furthermore, because the above by-produced 1,1-bis(p-isobutylphenyl)ethylene has a close boiling point, it is impossible to separate it from the unreacted 1,1-diarylethane by means of the conventional separation method such as distillation. Therefore, when the fraction mainly containing 1,1-bis(p-isobutylphenyl)ethane recovered in the step (II) is used intact again as the material for cracking in the cracking step (I), the properties of the obtained aimed product of p-isobutylstyrene are not suitable for the objects of uses in addition to the defect that the deterioration of cracking catalyst is rapid because of complicated cracked products of bis(isobutylphenyl)ethylene.

In view of the above facts, the inventors made investigations on the reuse of recovered 1,1-bis(p-isobutylphenyl)ethane fraction and other 1,1-diarylethane fractions, and it was found out that these fractions can be reused in the step (I) as a cracking material without any disadvantage by hydrogenating the diarylethylenes contained in the fractions into 1,1-diarylethanes.

The cracking of diarylethylene such as bis(isobutylphenyl)ethylene is complicated because they have carbon-carbon double bonds between two benzene rings which are easy to crack. The selective hydrogenation of diarylethylene is, therefore, preferred.

In the step (III) of the present invention, the fraction mainly containing 1,1-diarylethane obtained in the separation step (II) is brought into contact with hydrogen gas in the presence of a hydrogenating catalyst, thereby converting the olefin moiety of diarylethylene produced by the side reaction in the step (II) into paraffin structure. In this step, therefore, it is important to select the reaction conditions so as to hydrogenate only said olefinic moiety, that is, to avoid that the aromatic rings in 1,1-diarylethane are not hydrogenated into cyclohexyl rings.

Accordingly, the hydrogenation catalyst mut be those which can hydrogenate the ethylenically unsaturated carbon-carbon double bonds but inactive to the nuclear hydrogenation of aromatic rings. Any of such known hydrogenation catalysts can be selected. More particularly, metallic catalysts containing Pd, Rh, Pt, Ni, Co, Mo or W can be used. These catalysts can be carried on a suitable carrier such as silica, silica-alumina or carbon. The conditions for the hydrogenation may be such that the hydrogenation of aromatic rings does not occur. Because several by-products are formed, usually as a whole, the index for degree of hydrogenation may be 1.0 or lower, preferably 0.5 or lower, in bromine number for the efficiency of the cracking catalyst in the step (I). The temperature for the hydrogenation is in the range of room temperature to 300° C. The pressure is in the range of atmospheric pressure to 300 kg/cm².

After the hydrogenation of the step (III), the lighter fraction can be removed by distillation, if necessary.

The fraction mainly containing 1,1-diarylethane that is obtained through the hydrogenation of step (III) is returned to the cracker of the step (I) and cracked again. The thus obtained arylethylene has satisfactory properties for the purpose of uses.

The step (III) can be carried out with regard to the fraction itself which mainly contains 1,1-diarylethane obtained in the step (II). Or, the step (III) can be carried out after mixing fresh 1,1-diarylethane to be fed to the step (I) with the fraction mainly containing 1,1-diarylethane recovered in the step (II). Anyhow, the hydrogenated fraction is returned to the foregoing cracking step (I) and it is cracked again likewise, in which similar product can be obtained.

The hydrogenation fraction of the step (III) can be cracked again singly or in a mixture with fresh 1,1-diarylethane to be fed to the step (I).

Each step in the method of the present invention can be carried out either separately or continuously as a whole. Furthermore, any one of or the whole of the steps can be carried out batchwise.

Incidentally, as described in the foregoing passage, a medicine of highly pure ibuprofen can be prepared by subjecting the typically preferred arylethylene of p-isobutylstyrene to hydroformylation or hydroesterification. In the following, the preparation of ibuprofen from p-isobutylstyrene will be described.

In the hydroformylation, p-isobutylstyrene is converted into its aldehyde by a transition metal complex catalyst and the aldehyde is then oxidized to obtain the ibuprofen.

As the transition metal complex catalysts used for the hydroformylation of p-isobutylstyrene are exemplified by the metal complex catalysts containing active metals such as Pt, Rh, Ir, Ru, Co and Ni. With regard to the oxidation number of precious metals, any of those of zero to the maximum oxidation number can be used and metal complexes having ligands of halogen atoms, trivalent phosphorus compounds, π-allyl group, amines, nitriles, oximes, olefins, and carbon monoxide are effective.

The more particular examples of the above catalysts are bistriphenylphosphine dichlorocomplex, bistributylphosphine dichlorocomplex, bistricyclohexylphosphine dichlorocomplex, π-allyltriphenylphosphine dichlorocomplex, triphenylphosphine piperidine dichlorocomplex, bisbenzonitrile dichlorocomplex, biscyclohexyloxime dichlorocomplex, 1,5,9-cyclododecatriene dichlorocomplex, bistriphenylphosphine dicarbonyl complex, bistriphenylphosphine diacetate complex, bistriphenylphosphine dinitrate complex, bistriphenylphosphine sulfate complex, tetrakistriphenylphosphine complex; and complexes in which a part of ligands are carbon monoxide such as chlorocarbonyl bistriphenylphosphine complex, hydridocarbonyl tristriphenylphosphine, bischlorotetracarbonyl complex and dicarbonyl acetylacetonate complex, of the above-mentioned metals.

Furthermore, compounds which produce the above metal complexes in the reaction system can be also used.

That is, phosphine, nitrile, allyl compound, amine, oxime, olefin or carbon monoxide which is able to be the ligands to the oxides, sulfates or chlorides of the above transition metals, are simultaneously added into the reaction system.

The above phosphines are exemplified by triphenylphosphine, tritolylphosphine, tributylphosphine, tircyclohexylphosphine and triethylphosphine. The nitriles are exemplified by benzonitrile, acrylonitrile, propionitrile and benzylnitrile. The allyl compounds are exemplified by allyl chloride and allyl alcohol. The amines are exemplified by benzylamine, pyridine, piperazine and tri-n-butylamine. The oximes are exemplified by cyclohexyloxime, acetoxime and benzaldoxime. The olefins are exemplified by 1,5-cyclooctadiene and 1,5,9-cyclodecatriene.

In order to improve the rate of reaction, it is possible to add inorganic halides such as hydrogen chloride and boron trifluoride and organic iodides such as methyl iodide.

The addition quantity of these halides is 0.1 to 30 times by mole, preferably 1 to 15 times by mole as halogen atom relative to 1 mole of the transition metal complex catalyst or the active metal compounds. Even though the effect of addition depends upon the kind of used catalyst, when the addition quantity is less than 0.1 time by mole, the effect of the addition cannot be produced. On the other hand, when the addition quantity exceeds 30 times by mole, the catalytic activity is rather reduced, in addition, some side reaction other than the aimed reaction is caused to occur such as the halogen addition to the double bonds of p-isobutylstyrene.

The use quantity of the transition metal complex catalyst or the active metal compound which can produce a transition metal catalyst in this step is 0.0001 to 0.5 mole, preferably 0.001 to 0.1 mole to one mole of p-isobutylstyrene. When the active metal compound is used, the addition quantity of the compound to form ligands is 0.8 to 10 moles, preferably 1 to 4 moles to 1 mole of the active metal compound.

The hydroformylation reaction is carried out at temperatures in the range of 40° to 200° C., preferably 50° to 180° C. If the reaction temperature is below 40° C., the rate of reaction is very low which is not acceptable in industrial production process. On the other hand, if the reaction temperature is above 200° C., it is not desirable because the side reactions of polymerization and the decomposition of transition metal complex catalyst are caused to occur.

The reaction pressure can be selected arbitrary if it is 5 kg/cm² or above. At a pressure below 5 kg/cm², the rate of reaction is very small in view of practical working. If the pressure is high, it is desirable because the reaction can proceed rapidly. However, there is naturally its upper limit because a very high pressure requires the very high pressure resistance of reaction apparatus. In practice, a pressure as high as 500 kg/cm² is sufficient.

In the hydroformylation, it is sufficient to continue the reaction until the lowering of pressure owing to the absorption of the mixed gas of hydrogen and carbon monoxide is ceased. The duration of reaction of 4 to 20 hours is generally sufficient.

The carbon monoxide and hydrogen that are necessary for the hydroformylation can be fed either separately or by mixing them previously. The molar ratio of carbon monoxide and hydrogen to be fed into the reaction system can be selected arbitrary. In this hydroformylation reaction, carbon mnoxide and hydrogen are consumed at a molar ratio of 1:1. Accordingly, as the gas supplied in excess remains unreacted, the reaction is caused to proceed again when the other gas is supplied at the time when the lowering of pressure is ceased and reactants still remain. Even though the effect of reaction depends upon the size of reaction vessel and the mode of reaction, it is generally most effective that carbon monoxide and hydrogen are fed in a molar ratio of 1:1.

In addition to the above described feed of reactant gases, an inert gas can coexist in the hydroformylation reaction.

In the hydroformylation of the present invention, it is possible to use an inert solvent in order to remove the heat of reaction. The solvents which are inert to the hydroformylation are exemplified by polar solvents such as ethers, ketones and alcohols, and nonpolar solvents such as paraffins, cycloparaffins and aromatic hydrocarbons. However, satisfactory result can be generally obtained without any solvent.

After the hydroformylation, the obtained α-(4-isobutylphenyl)propionaldehyde is oxidized by the conventional method using, for example, permanganate or hypochlorite to obtain the ibuprofen, α-(4-isobutylphenyl)propionic acid.

In the following, the method to convert p-isobutylstyrene into α-(4-isobutylphenyl)propionic acid using precious metal complex catalyst by the hydroesterification will be described.

The precious metal complex catalysts used for the hydroesterification are exemplified by the precious metal complexes of Pd, Rh and Ir, especially the complex of Pd. The metals having ligands of halogen atoms, trivalentphosphorus compounds or carbonyl complexes can be used. A precious metal, for example, palladium of zero-valent to divalent is used.

The more particular examples of the above catalysts are bistriphenylphosphine dichloropalladium, bistributylphosphine dichloropalladium, bistricyclohexylphosphine dichloropalladium, π-allyltriphenylphosphine chloropalladium, triphenylphosphine piperidine dichloropalladium, bisbenzonitrile dichloropalladium, biscyclohexyloxime dichloropalladium, 1,5,9-cyclododecatriene dichloropalladium, bistriphenylphosphine dicarbonylpalladium, bistriphenylphosphine palladium acetate, bistriphenylphosphine palladium nitrate, bistriphenylphosphine palladium sulfate, and tetrakistriphenylphosphine palladium.

Furthermore, the catalysts can be used by adding it to the reaction system or the complex is formed in the reaction system by adding separately a compound to be ligands to the reaction system.

The use quantity of catalyst is 0.0001 to 0.5 mole, preferably 0.001 to 0.1 mole to 1 mole of p-isobutylstyrene. The addition quantity of the compound to form ligands is 0.8 to 10 moles, preferably 1 to 4 moles to 1 mole of a precious metal to form the nuclei of complex of Pd, Rh or Ir.

The hydroesterification reaction is carried out at temperatures in the range of 40° to 150° C., preferably 70° to 120° C. The pressure of carbon monoxide is 30 to 700 kg/cm², preferably 90 to 500 kg/cm². In order to accelerate the reaction, an acid such as hydrogen chloride or boron trifluoride can be added.

In the hydroesterification, when p-isobutylstyrene is allowed to react in the presence of water, a carboxylic acid of α-(4-isobutylphenyl)propionic acid is obtained. When it is allowed to react in the presence of a lower alcohol having any alkyl group, a lower alkyl ester of α-(4-isobutylphenyl)propionic acid is obtained. For example, a methyl ester is obtained with methyl alcohol.

The alcohols are exemplified by lower alcohols such as methyl alcohol, ethyl alcohol, n-propyl alcohol, isopropyl alcohol, n-butyl alcohol, sec-butyl alcohol, tert-butyl alcohol and isobutyl alcohol having 1 to 4 carbon atoms. Among them, methyl alcohol is preferable.

After the hydroesterification, the aimed compound of α-(4-isobutylphenyl)propionic acid or its alkyl ester and catalyst can be separated by distilling the reaction product, preferably under a reduced pressure. The recovered complex catalyst can be used again.

When an alkyl ester of α-(4-isobutylphenyl)propionic acid is obtained, α-(4-isobutylphenyl)propionic acid can be prepared by the hydrolysis of the former compound according to an ordinary method.

As described above, the deterioration of cracking catalyst with the passage of time can be prevented according to the method of the present invention for producing highly pure arylethylene by cracking 1,1-diarylethane. Therefore, unreacted material can be re-used and industrial working can be carried out economically.

Because the arylethylene prepared by the method of the present invention is highly pure, the preferable arylethylene of p-isobutylstyrene can be used as an intermediate material for preparing a valuable medicine of ibuprofen by carbonylation in the presence of a transition metal complex catalyst. Furthermore, the arylethylene is also suitable as the monomer for use in radical polymerization or copolymerization.

In the following, the present invention will be described in more detail with reference to examples.

EXAMPLE 1

Synthesis of p-Isobutylstyrene by Cracking 1,1-Bis(p-isobutylphenyl)ethane

Isobutylbenzene was reacted with acetaldehyde in the presence of sulfuric acid catalyst to obtain a fraction of 1,1-bis(p-isobutylphenyl)ethane (bromine number=0.16) having a boiling range of 177° to 184° C. at a reduced pressure of 2 to 3 mmHg. This fraction was subjected to the following cracking step (I), separation step (II) and hydrogenation step (III).

Step (I): Cracking Reaction

A silica-alumina catalyst N-631-L (trademark, made by Nikki Chemical Corp., size: 15–25 mesh) was fed into a stainless steel reaction tube of 12 mm in inner diameter. The height of the filled catalyst was 135 mm. This was heated to 500° C. by an electric furnace and cracking was carried out by feeding continuously 15 ml/hr of 1,1-bis(p-isobutylphenyl)ethane and 170 ml/hr of water. After cooling the outlet of the reaction tube, the oily layer was separated and it was analyzed by gas chromatography. The results are shown in the following.

| Results of Gas Chromatographic Analysis (1) | |
|---|---|
| Lighter fraction | 2.7 wt. % |
| Isobutylbenzene fraction | 24.6 wt. % |
| p-Isobutylethylbenzene fraction | 2.3 wt. % |
| p-Isobutylstyrene fraction | 24.8 wt. % |
| Unreacted 1,1-bis(p-isobutylphenyl)-ethane fraction | 44.3 wt. % |
| Heavier fraction | 1.3 wt. % |
| Average rate of cracking | 55.1% |

Step (II): Separation

The cracking product obtained in the cracking step (I) was subjected to precise fractional distillation under ordinary distillation conditions (distillation was carried out likewise also in the following examples). By this distillation, a p-isobutylstyrene fraction having a boiling range of 74° to 89° C. under reduced pressure of 3 to 4 mmHg and an unreacted 1,1-bis(p-isobutylphenyl)ethane recovery fraction having a boiling range of 175° to 185° C. were obtained. The recovery rate of the former fraction was 73% and that of the latter fraction was 91%.

The bromine number of the recovered 1,1-bis(p-isobutylphenyl)ethane fraction was 3.5. According to mass spectrometry, the content of component of $m/e = 292$ was 6.0% (m/e of 1,1-bis(p-isobutylphenyl)ethane is 294). It was confirmed that the component of $m/e = 292$ was mainly bis(isobutylphenyl)ethylene by G.C. and G.C. mass spectrometric analysis.

Step (III): Hydrogenation Treatment

A palladium catalyst G-68B (trademark, made by Nissan Girdler, size: 20–25 mesh) was fed into a stainless steel reaction tube of 10 mm in inner diameter. The height of the filled catalyst was 80 mm. This was heated to 180° C. by an electric furnace and hydrogenation was carried out by feeding 10 ml/hr of 1,1-bis(p-isobutylphenyl)ethane fraction recovered in the separation step (II) and 200 ml/hr of hydrogen. This hydrogenation was carried out under a pressure of 12 kg/cm².

The bromine number of the treated 1,1-bis(p-isobutylphenyl)ethane fraction was 0.18. According to mass spectrometry, the content of component of $m/e = 292$ was less than 0.5%.

EXAMPLE 2

Cracking of Hydrogenated 1,1-Bis(p-isobutylphenyl)ethane Fraction

The 1,1-bis(p-isobutylphenyl)ethane fraction obtained by the hydrogenation step (III) in Example 1, was subjected to cracking in the like manner as in the step (I) of Example 1 and the cracking product was then treated by precise fractional distillation in the like manner as the separation step (II) of Example 1 to obtain p-isobutylstyrene fraction and 1,1-bis(p-isobutylphenyl)ethane fraction. The recovery rates of these fractions were almost the same as those in Example 1. The results of analysis with regard to the reaction products are shown in the following.

| Results of Gas Chromatographic Analysis (2) | |
|---|---|
| Lighter fraction | 2.6 wt. % |
| Isobutylbenzene fraction | 23.0 wt. % |
| p-Isobutylethylbenzene fraction | 2.2 wt. % |
| p-Isobutylstyrene fraction | 23.7 wt. % |
| Unreacted 1,1-bis(p-isobutylphenyl)ethane fraction | 47.2 wt. % |
| Heavier fraction | 1.3 wt. % |
| Average rate of cracking | 52.2% |

The bromine number of the recovered 1,1-bis(p-isobutylphenyl)ethane was 3.0. According to mass spectrometry, the content of component of $m/e = 292$ was 5.5%.

COMPARATIVE EXAMPLE 1

Re-cracking of Recovered 1,1-Bis(p-isobutylphenyl)ethane Fraction

The 1,1-bis(p-isobutylphenyl)ethane fraction recovered in the step (II) of Example 1 was used intact, i.e. without hydrogenation treatment, and cracked in the like manner as in the step (I) of Example 1 and the obtained product was then treated by precise fractional distillation in the like manner as the step (II) of Example 1 to obtain a p-isobutylstyrene fraction and 1,1-bis(p-isobutylphenyl)ethane fraction. The recovery rates of these fractions were almost the same as those in Examples. The results of analysis with regard to the reaction products are shown in the following.

| Results of Gas Chromatographic Analysis (3) | |
|---|---|
| Lighter fraction | 1.1 wt. % |
| Isobutylbenzene fraction | 19.2 wt. % |
| p-Isobutylethylbenzene fraction | 1.9 wt. % |
| p-Isobutylstyrene fraction | 19.4 wt. % |
| Unreacted 1,1-bis(p-isobutylphenyl)ethane fraction | 56.3 wt. % |
| Heavier fraction | 2.1 wt. % |
| Average rate of cracking | 42.5% |

The bromine number of the recovered 1,1-bis(p-isobutylphenyl)ethane was 4.6. According to mass spectrometry, the content of component of $m/e = 292$ was 8.5%.

The changes in cracking rates with the passage of time in Examples 1 and 2 and Comparative Example 1 are shown in the following Table 1.

TABLE 1

| Comparison of Changes in Cracking Rates (%) | | | |
|---|---|---|---|
| Example | 24 Hours | 48 Hours | 72 Hours |
| Example 1 | 100 | 100 | 100 |
| Example 2 | 101 | 98 | 100 |
| Comp. Ex. 1 | 97 | 80 | 75 |

(The values in Table 1 are the proportions when the cracking rates at the respective hours in Example 1 are regarded as 100.)

As will be understood from Table 1, when the re-cracking is done without hydrogenation, the life of cracking catalyst is very short. In other words, it is apparent that the fraction obtained after the cracking cannot be recycled without any treatment. However, when the fraction is hydrogenated, it can be reused satisfactorily, which fact can make the cracking process of the present invention advantageous.

EXAMPLE 3

Hydroformylation of p-Isobutylstyrene Fraction (1)

Hydroformylation was carried out using the p-isobutylstyrene fractions obtained in Examples 1 and 2 and Comparative Example 1.

To a 250 ml autoclave with a stirrer were added 30 g of p-isobutylstyrene fraction and 40 g of toluene and the contents were maintained at 60° C. An equimolar mixture of hydrogen and carbon monoxide was then fed to the autoclave to a pressure of 70 kg/cm² and reaction was continued for 16 hours. After the reaction, the reaction mixture was cooled to room temperature and the remaining mixed gas was discharged. The contents were analyzed by gas chromatography to obtain the rate of reaction.

In the above reaction, 0.0001 mole of rhodium tristriphenylphosphine and 0.001 mole of triphenylphosphine were used for the p-isobutylstyrene fraction.

TABLE 2

| | Results of Hydroformylation (p-Isobutylstyrene) | |
|---|---|---|
| Example | Reaction Rate | Selectivity Coeff. |
| Example 1 | 97 | 11 |
| Example 2 | 96 | 13 |
| Comp. Ex. 1 | 57 | 1 |

Notes:
Reaction Rates:
Molar % relative to the fed p-isobutylstyrene calculated from the remained p-isobutylstyrene after the reaction.
Selectivity Coefficient:
Molar % of α-phenyl compound to β-phenyl compound of p-isobutylphenylpropionaldehyde as carbonylation product.

Notes

Reaction Rates:
Molar % relative to the fed p-isobutylstyrene calculated from the remained p-isobutylstyrene after the reaction.
Selectivity Coefficient:
Molar % of α-phenyl compound to β-phenyl compound of p-isobutylphenylpropionaldehyde as carbonylation product.

EXAMPLE 4

Hydroesterification of p-Isobutylstyrene Fraction (2)

Hydroesterification was carried out using the p-isobutylstyrene fractions obtained in Examples 1 and 2 and Comparative Example 1.

To a 250 ml autoclave with a stirrer were added 30 g of p-isobutylstyrene fraction, 40 g of toluene and 15 g of methanol and the contents were maintained at 90° C. Carbon monoxide was then fed to the autoclave to a pressure of 80 kg/cm² and reaction was continued for 16 hours. After the reaction, the reaction mixture was cooled to room temperature and the remaining gas was discharged. The contents were analyzed by gas chromatography to obtain the rate of reaction.

In the above reaction, 0.0003 mole of dichloropalladium tristriphenylphosphine and 0.0015 mole of triphenylphosphine were used for the p-isobutylstyrene fraction.

TABLE 3

| | Results of Hydroesterification (p-Isobutylstyrene) | |
|---|---|---|
| Example | Reaction Rate | Selectivity Coeff. |
| Example 1 | 89 | 11 |
| Example 2 | 91 | 12 |
| Comp. Ex. 1 | 74 | 6 |

Notes:
Reaction Rates:
The same as Table 2.
Selectivity Coefficient:
Molar % of α-phenyl compound to β-phenyl compound of p-isobutylphenylpropionic acid methyl ester as carbonylation product.

Notes

Reaction Rates:
The same as Table 2.
Selectivity Coefficient:
Molar % of α-phenyl compound to β-phenyl compound of p-isobutylphenylpropionic acid methyl ester as carbonylation product.

EXAMPLE 5

Synthesis of Styrene by Cracking of 1,1-Diphenylethane

Step (I): Cracking Reaction

A silica-alumina catalyst N-631-L (15–25 mesh) was fed into a stainless steel reaction tube of 12 mm in inner diameter. The height of the filled catalyst was 135 mm. This was heated to 500° C. by an electric furnace and cracking was carried out by feeding continuously 15 ml/hr of 1,1-diphenylethane (bromine number: 0.020) and 150 ml/hr of water. After cooling the outlet of the reaction tube, the oily layer was separated and analyzed by gas chromatography. The results are shown in the following.

| Results of Gas Chromatographic Analysis (4) | |
|---|---|
| Lighter fraction | 1.9 wt. % |
| Benzene fraction | 18.8 wt. % |
| Ethylbenzene fraction | 1.5 wt. % |
| Styrene fraction | 23.0 wt. % |
| Unreacted 1,1-diphenylethane fraction | 53.9 wt. % |
| Heavier fraction | 0.9 wt. % |
| Average rate of cracking | 45.6% |

Step (II): Separation

The cracking product obtained in the cracking step (I) was subjected to precise fractional distillation under ordinary distillation conditions. By this distillation, a styrene fraction (meaning the fraction mainly containing styrene, this is applied to the following passages likewise) having a distilling temperature range of 54° to 58° C. under reduced pressure of 30 to 35 mmHg and an unreacted 1,1-diphenylethane recovery fraction having a distillation temperature range of 148° to 155° C. were obtained. The recovery rate of the styrene fraction was 85% and that of unreacted 1,1-diphenylethane recovery fraction was 93%.

The bromine number of the recovered 1,1-diphenylethane fraction was 2.37. According to mass spectrometry, the content of component of $m/e=180$ was 2.5% (m/e of 1,1-diphenylethane is 182).

Step (III): Hydrogenation Treatment

A palladium catalyst G-68B (20–25 mesh) was fed into a stainless steel reaction tube of 10 mm in inner diameter. The height of the filled catalyst was 80 mm. This was heated to 180° C. by an electric furnace and hydrogenation was carried out by feeding 10 ml/hr of 1,1-diphenylethane fraction obtained in the separation step (II) and 200 ml/hr of hydrogen. This hydrogenation was carried out under a pressure of 12 kg/cm².

The bromine number of the treated 1,1-diphenylethane fraction was 0.17. According to mass spectrometry, the content of component of $m/e=180$ was less than 0.5%.

EXAMPLE 6

Cracking of Hydrogenated 1,1-Diphenylethane Fraction

The 1,1-diphenylethane fraction obtained by the hydrogenation step (III) in Example 5, was subjected to cracking in the like manner as in the step (I) of Example 5 and the cracking product was then treated by precise fractional distillation in the like manner as the separation step (II) of Example 5 to obtain a styrene fraction and 1,1-diphenylethane fraction. The recovery rates of these fractions were almost the same as those in Example 5. The results of analysis with regard to the reaction products are shown in the following.

| Results of Gas Chromatographic Analysis (5) | |
|---|---|
| Lighter fraction | 2.1 wt. % |
| Benzene fraction | 19.6 wt. % |
| Ethylbenzene fraction | 1.3 wt. % |
| Styrene fraction | 21.5 wt. % |
| Unreacted 1,1-diphenylethane fraction | 54.3 wt. % |
| Heavier fraction | 1.2 wt. % |
| Average rate of cracking | 45.0% |

The bromine number of the recovered 1,1-diphenylethane was 2.54. According to mass spectrometry, the content of component of $m/e=180$ was 2.5%.

COMPARATIVE EXAMPLE 2

Re-cracking of 1,1-Diphenylethane Recovered Fraction

The 1,1-diphenylethane fraction recovered in the step (II) of Example 5 was used intact, i.e. without hydrogenation treatment, and cracked in the like manner as in the step (I) of Example 5 and the product of cracking was then treated by precise fractional distillation in the like manner as the step (II) of Example 5 to obtain a styrene fraction and 1,1-diphenylethane fraction. The recovery rates of these fractions were almost the same as those in Examples. The results of analysis with regard to the reaction products are shown in the following.

| Results of Gas Chromatographic Analysis (6) | |
|---|---|
| Lighter fraction | 1.5 wt. % |
| Benzene fraction | 14.3 wt. % |
| Ethylbenzene fraction | 1.2 wt. % |
| Styrene fraction | 16.6 wt. % |
| Unreacted 1,1-diphenylethane fraction | 65.6 wt. % |
| Heavier fraction | 0.8 wt. % |
| Average rate of cracking | 33.9% |

The bromine number of the recovered 1,1-diphenylethane was 4.22. According to mass spectrometry, the content of component of $m/e=180$ was 4.7%.

The changes in cracking rates with the passage of time in Examples 5 and 6 and Comparative Example 2 are shown in the following Table 4.

TABLE 4

| Comparison of Changes in Cracking Rates (%) | | | |
|---|---|---|---|
| Example | 24 Hours | 48 Hours | 72 Hours |
| Example 5 | 100 | 100 | 100 |
| Example 6 | 99 | 101 | 99 |
| Comp. Ex. 2 | 98 | 81 | 73 |

(The values in Table 4 are the proportions when the cracking rates at the respective hours in Example 5 are regarded as 100.)

EXAMPLE 7

Preparation of Dimethylstyrene by Cracking 1,1-Di(o-xylyl)ethane o-Xylene and acetaldehyde were reacted in the presence of sulfuric acid catalyst. The obtained 1,1-di(o-xylyl)ethane fraction (bromine number=0.27) of 146° to 151° C. in distillation temperature at a reduced pressure of 3 to 5 mmHg was subjected to cracking step (I) and separation step (II) in the like manner as Example 5. The average cracking rate was 47.3%.

The cracking product was subjected to precise fractional distillation to obtain a dimethylstyrene fraction of 67° to 70° C. in distillation temperature at a reduced pressure of 10 to 12 mmHg (recovery rate: 78%), and 1,1-di(o-xylyl)ethane fraction of 129° to 137° C. in distillation temperature at a reduced pressure of 2 to 3 mmHg (recovery rate: 91%). The bromine number of the recovered 1,1-di(o-xylyl)ethane fraction was 2.17 and, according to mass spectrometry, 3.0% of the component of $m/e=236$ was contained (m/e of 1,1-di(o-xylyl)ethane is 238).

Recovered 1,1-di(o-xylyl)ethane was subjected to hydrogenation in the like manner as in the step (III) of Example 5 to obtain a treated fraction of 0.21 in bromine number.

EXAMPLE 8

Preparation of Dimethylstyrene from Hydrogenated Fraction

The hydrogenated 1,1-di(o-xylyl)ethane fraction obtained in Example 7 was subjected to cracking in the like manner as in the cracking step (I) of Example 5 (average cracking rate: 46.9%), and a dimethylstyrene fraction with a recovery rate of 76% and 1,1-di(o-xylyl)ethane fraction with a recovery rate of 89% were obtained.

The bromine number of the recovered 1,1-di(o-xylyl)ethane fraction was 2.65 and, according to mass spectrometry, 3.5% of the component of $m/e=236$ was contained.

COMPARATIVE EXAMPLE 3

Preparation of Dimethylstyrene from Non-treated Fraction

The 1,1-di(o-xylyl)ethane fraction recovered by the precision fractional distillation in Example 7 was used intact for cracking in the like manner as in Example 5 (average cracking rate: 32.1%) and the cracking product was then treated likewise by precise fractional distillation to obtain a dimethylstyrene fraction and 1,1-di(o-xylyl)ethane fraction. The recovery rates of these fractions were almost the same as those in Example 7.

The bromine number of recovered 1,1-di(o-xylyl)ethane was 4.37. According to mass spectrometry, the content of the component of $m/e=236$ was 4.5%.

EXAMPLE 9

Preparation of t-butylstyrene by Cracking 1,1-Bis(p-t-butylphenyl)ethane t-Butylbenzene and acetaldehyde were reacted in the presence of sulfuric acid catalyst. The obtained 1,1-bis(p-t-butylphenyl)ethane fraction (bromine number=0.17) of 96° to 97° C. in distillation temperature at a reduced pressure of 2 to 3 mmHg was subjected to the cracking step (I) and the separation step (II) in the like manner as Example 5. The average cracking rate was 40.8%.

The cracking product was subjected to precise fractional distillation to obtain a t-butylstyrene fraction of 79° to 83° C. in distillation temperature at a reduced pressure of 6 to 8 mmHg (recovery rate: 73%), and 1,1-bis(p-t-butylphenyl)ethane fraction of 159° to 166° C. in distillation temperature at a reduced pressure of 2 to 3 mmHg (recovery rate: 92%). The bromine number of the recovered 1,1-bis(p-t-butylphenyl)ethane fraction was 2.17 and, according to mass spectrometry, 4.0% of the component of $m/e = 292$ was contained ($m/e$ of 1,1-bis(p-t-butylphenyl)ethane is 294).

Recovered 1,1-bis(p-t-butylphenyl)ethane was subjected to hydrogenation in the like manner as in Example 5 to obtain a treated fraction of 0.18 in bromine number.

EXAMPLE 10

Preparation of p-t-Butylstyrene from Hydrogenated Fraction

The hydrogenated 1,1-bis(p-t-butylphenyl)ethane fraction obtained in Example 9 was subjected to cracking in the like manner as in the cracking step (I) of Example 5 (average cracking rate: 38.9%), and a p-t-butylstyrene fraction with a recovery rate of 74% and 1,1-bis(p-t-butylphenyl)ethane fraction with a recovery rate of 89% were obtained.

The bromine number of the recovered 1,1-bis(p-t-butylphenyl)ethane fraction was 1.98 and, according to mass spectrometry, 3.5% of the component of $m/e = 292$ was contained.

COMPARATIVE EXAMPLE 4

Preparation of p-t-Butylstyrene from Non-treated Fraction

The 1,1-bis(p-t-butylphenyl)ethane fraction recovered by the precision fractional distillation in Example 9 was used intact for cracking in the like manner as in Example 5 (average cracking rate: 27.2%) and the cracking product was then treated likewise by precise fractional distillation to obtain a t-butylstyrene fraction and 1,1-bis(p-t-butylphenyl)ethane fraction. The recovery rates of these fractions were almost the same as those in Example 9.

The bromine number of the recovered 1,1-bis(p-t-butylphenyl)ethane was 3.81. According to mass spectrometry, the content of the component of $m/e = 292$ was 7.5%.

EXAMPLE 11

Copolymerization with Styrenes, Preparation of Resin Films and Comparison of Light Stability Each of styrene fractions obtained in Examples 5 to 10 and Comparative Examples 2 to 4 was polymerized to prepare resin films and the light stability of them was compared.

A polymerization initiator of di-t-butyl peroxide was added to each styrene fraction and the fraction was heated to 60° C. and left to stand still for 12 hours with heating to obtain resinous substance.

The obtained resin was dissolved in benzene and the solution was applied to the surfaces of glass plates so as to form 0.2 mm thick film. The glass plates were dried at 65° C. for 4 hours in a thermostat to obtain resin films on the glass plates.

Three resin films for each styrene fraction were irradiated by ultraviolet rays at 70° C. and the changes of the surfaces of resin films were observed to make comparison of light stability. The changes of surfaces were checked by the color change of resin films and the formation of cracks in the surfaces of resin films.

TABLE 5

| Styrenes | Example | After 7 Days | After 1 Month |
|---|---|---|---|
| Styrene | Example 5 | O | O |
|  | Example 6 | O | O |
|  | Comp. Ex. 2 | O | X |
|  | Example 7 | O | O |
| Dimethylstyrene | Example 8 | O | O |
|  | Comp. Ex. 3 | O | + |
|  | Example 9 | O | O |
| t-Butylstyrene | Example 10 | O | O |
|  | Comp. Ex. 4 | O | + |

Notes:
O: No change in color and surface condition was observed in resin films.
+: Yellowing and/or surface cracks were observed in resin films.
X: Serious yellowing and/or surface cracks were observed in resin films.

Notes

O: No change in color and surface condition was observed in resin films.

+: Yellowing and/or surface cracks were observed in resin films.

X: Serious yellowing and/or surface cracks were observed in resin films.

EXAMPLE 12

Hydroformylation of Styrene Fraction

Hydroformylation was carried out using the styrene fractions obtained in Examples 5 to 10 and Comparative Examples 2 to 4.

To a 250 ml autoclave with a stirrer were added 30 g of styrene fraction and 40 g of toluene and the contents were maintained at 60° C. An equimolar mixture of hydrogen and carbon monoxide was then fed to the autoclave to a pressure of 70 kg/cm² and reaction was continued for 16 hours. After the reaction, the reaction mixture was cooled to room temperature and the remaining mixed gas was discharged. The contents were analyzed by gas chromatography to obtain the rate of reaction.

In the above reaction, 0.0001 mole of rhodium hydridocarbonyltristriphenylphosphine and 0.001 mole of triphenylphosphine were used for the styrene fractions.

TABLE 6

| Styrenes | Hydroformylation Reaction | | |
|---|---|---|---|
|  | Example | Reaction Rate | Select. Coeff. |
| Styrene | Example 5 | 97 | 13 |
|  | Example 6 | 95 | 14 |
|  | Comp. Ex. 2 | 67 | 5 |
|  | Example 7 | 97 | 11 |
| Dimethylstyrene | Example 8 | 94 | 9 |
|  | Comp. Ex. 3 | 72 | 4 |
|  | Example 9 | 98 | 12 |
| t-Butylstyrene | Example 10 | 98 | 11 |
|  | Comp. Ex. 4 | 67 | 5 |

Notes:
Reaction Rates:
Molar % relative to the fed styrene fraction calculated from the remained styrene fraction after the reaction.
Selectivity Coefficient:
Molar % of α-phenyl compound to β-phenyl compound of aryl propionaldehyde as hydroformylation product.

Notes

Reaction Rates:
Molar % relative to the fed styrene fraction calculate from the remained styrene fraction after the reaction.
Selectivity Coefficient:

Molar % of α-phenyl compound to β-phenyl compound of aryl propionaldehyde as hydroformylation product.

What is claimed is:

1. A method for producing arylethylene which method comprises the steps of (I), (II), (III) and (IV):

step (I): bringing 1,1-diarylethane represented by the following general formula (A) into contact with an acid catalyst in the presence of an inert gas to crack said 1,1-diarylethane into arylethylenes represented by the general formulae (B) and/or (C) and alkylbenzenes represented by the general formulae (D) and/or (E);

step (II): separating the reaction mixture obtained in the above cracking step (I) into at least a fraction mainly containing 1,1-diarylethane of the general formula (A);

step (III): bringing said fraction mainly containing 1,1-diarylethane of the general formula (A) into contact with hydrogen gas in the presence of a hydrogenation catalyst to hydrogenate diarylethylene contained therein into 1,1-diarylethane; and step (IV): re-cracking hydrogenated fraction obtained in the preceding hydrogenation step (III) by bringing it into said cracking step (I), General formula (A): $Ar_1$—$CH(CH_3)$—$Ar_2$
General formula (B): $Ar_1$—$CH$=$CH_2$
General formula (C): $Ar_2$—$CH$=$CH_2$
General formula (D): $Ar_1$—H
General formula (E): $Ar_2$—H wherein each of $Ar_1$ and $Ar_2$ in the above general formulae (A), (B), (C), (D) and (E) is a phenyl group or an alkylphenyl group having a hydrogen atom or one or a plurality of the same or different alkyl groups having 4 or less carbon atoms and the total number of carbon atoms is 4 or less and $Ar_1$ and $Ar_2$ can be the same or different ones.

2. The method for producing arylethylene in claim 1, wherein said arylethylene is p-isobutylstyrene, which method comprises the steps of (I), (II), (III) and (IV):

step (I): bringing 1,1-bis(p-isobutylphenyl)ethane into contact with an acid catalyst in the presence of an inert gas to crack said compound into p-isobutylstyrene and isobutylbenzene;

step (II): separating by distillation the reaction mixture obtained by said cracking step (I) into at least a fraction mainly containing 1,1-bis(p-isobutylphenyl)ethane;

step (III): bringing said fraction mainly containing unreacted 1,1-bis(p-isobutylphenyl)ethane into contact with hydrogen gas in the presence of a hydrogenation catalyst to hydrogenate bis-(isobutylphenyl)ethylene contained therein into 1,1-bis(isobutylphenyl)ethane; and step (IV): re-cracking hydrogenated fraction mainly containing 1,1-bis(p-isobutylphenyl)ethane obtained into the preceding hydrogenation step (III) by recycling it into said cracking step (I).

3. The method for producing arylethylene in claim 1 or 2, wherein said acid catalyst of the step (I) is selected from the group consisting of protonic acids, inorganic solid acids and protonic acids carried on an inorganic solid acid.

4. The method for producing arylethylene in claim 3, wherein said protonic acid is an inorganic protonic acid selected from the group consisting of phosphoric acid, sulfuric acid, hydrochloric acid and hetero-poly-acids.

5. The method for producing arylethylene in claim 3, wherein said protonic acid is an organic protonic acid selected from the group consisting of benzenesulfonic acid and toluenesulfonic acid.

6. The method for producing arylethylene in claim 3, wherein said inorganic solid acid is synthetic inorganic solid acid such as silica-alumina, silica-magnesia and zeolite, or natural inorganic solid acids such as activated clay, acid clay, kaolin and attapulgite.

7. The method for producing arylethylene in claim 3, wherein said protonic acid catalyst carried on said acid is a protonic acid catalyst with which an inorganic porous carrier such as non-acidic silica or alumina is impregnated.

8. The method for producing arylethylene in claim 1 or 2, wherein the temperature of contact with an acid catalyst is in the range of 200° to 650° C.

9. The method for producing arylethylene in claim 1 or 2, wherein said contact with an acid catalyst is gas phase contact.

10. The method for producing arylethylene in claim 1 or 2, wherein said hydrogenation catalyst of step (III) is a metallic catalyst containing Pd, Rh, Pt, Ni, Co, Mo or W.

11. The method for producing arylethylene in claim 1 or 2, wherein said hydrogenation of step (III) is carried out at a temperature within the range of room temperature to 300° C. and under a pressure within the range of atmospheric pressure to 300 kg/cm².

12. The method for producing arylethylene in claim 1 or 2, wherein the index for the degree of hydrogenation in said step (III) is 1.0 or lower in bromine number.

* * * * *